United States Patent [19]

Howard

[11] Patent Number: 4,466,216

[45] Date of Patent: Aug. 21, 1984

[54] METHOD FOR PROPAGATING PLANTS FROM TISSUE CULTURES

[75] Inventor: John A. Howard, Pacifica, Calif.

[73] Assignee: Stauffer Chemical Company, Westport, Conn.

[21] Appl. No.: 396,197

[22] Filed: Jul. 8, 1982

[51] Int. Cl.$^3$ .............................................. A01G 1/00
[52] U.S. Cl. ...................................................... 47/58
[58] Field of Search ............................ 435/241; 47/58

[56] References Cited

U.S. PATENT DOCUMENTS 3,816,960 6/1974 Gudin et al. .............................. 47/58
4,326,034 4/1982 Peel et al. ............................. 435/241

FOREIGN PATENT DOCUMENTS

WO81/3255 11/1981 PCT Int'l Appl. .
1401665 7/1975 United Kingdom .

OTHER PUBLICATIONS

Frontiers of Plant Tissue Culture, Thorpe, 1978, Intl-Assoc. Plant Tissue Culture, Univ. of Calgary, pp. 453–462.

Bergmann, "Wachstum grüner Suspensionskulturen", etc., Planta, vol. 74, 243–249, (1967).

Murashige, "Principles of Rapid Propagation", Symposium, U.S. Dept. of Energy, (K. W. Hughes et al., ed.), 1978.

Gathercole, et al., "Carbon Dioxide as an Essential Requirement", etc., Physiol. Plant, vol. 37, 213–217, (1976).

Stuart et al., "Studies on the Growth in Culture of Plant Cells", Journal of Exptl. Biology, vol. 22, No. 70, 96–106, (1971).

Cornejo-Martin et al., "Organ Redifferentiation in Rice Callus", Z. Pflanzenphysiologie, vol. 94, 117–123, (1979).

Kriedemann et al., "Vine Response to Carbon Dioxide Enrichment", Australian Journal of Plant Physiology, No. 3, 605–618, (1976).

Molnar et al., "Effect of Carbon Dioxide on Propagation of Softwood", Can. J. Plant Science, vol. 48, 495–499, (1968).

Mingo-Castel et al., "Effect of Carbon Dioxide and Ethylene . . . ", Plant Physiology, vol. 53, 798–801, (1974).

Murashige, "Plant Propagation Through Tissue Cultures", Ann. Rev. Plant Physiology, vol. 25, 135–166, (1974).

*Primary Examiner*—Robert E. Bagwill
*Attorney, Agent, or Firm*—Joel G. Ackerman

[57] ABSTRACT

Propagation of plants, particularly solanaceous plants, from tissue cultures is improved by the presence of exogenous carbon dioxide in the atmosphere.

4 Claims, No Drawings

METHOD FOR PROPAGATING PLANTS FROM TISSUE CULTURES

BACKGROUND AND PRIOR ART

This invention relates to a new method for propagating plants, particularly solanaceous plants, from tissue cultures, particularly from cotyledon explants and from callus cultures, grown on an appropriate nutrient medium, preferably with a carbohydrate, i.e. sugar, carbon source, and particularly in the presence of exogenous carbon dioxide.

Propagation of plants from tissue cultures is a well known technique and is summarized, for instance, in the paper "Principles of Rapid Propagation" by T. Murashige, in the symposium "Propagation of Higher Plants Through Tissue Culture: A Bridge Between Research and Application", United States Department of Energy, Technical Information Center, 1978 (K. W. Hughes, et al., editors), and in the article "Plant Propagation Through Tissue Cultures," *Annula Review of Plant Physiology*, Vol. 25, pp. 135–166, also by Murashige.

Similarly, the conditions for propagating plants from tissue cultures and by other means, and the factors involved, have been studied extensively through the years. The same is true for conditions of growing cell cultures. One of the factors which has been included in these studies from time to time is the effect of additional or exogenous carbon dioxide, that is, a quantity above the normal content of this substance in the atmosphere.

For instance, added carbon dioxide has been shown to be conducive to the propagation of certain plants from cuttings (Molnar, et al., *Canadian Journal of Plant Science*, Vol. 48, pp. 495–499, 1968) as well as the growth of roots in grapevines (Kriedemann, et al., *Australian Journal of Plant Physiology*, No. 3, pp. 605–618, 1976). Studies of the effect of carbon dioxide on tuberization of isolated potato stolons have also been conducted (Mingo-Castel, et al., *Plant Physiology*, Vol. 53, pp. 798–801, 1974).

The effect of carbon dioxide on the growth and properties of suspension cultures and other tissue cultures not intended for propagating plants has also been studied, for instance by Stuart, et al., *Journal of Experimental Botany*, Vol. 22, No. 70, pp. 96–106, (1971), Gathercole, et al., *Physiol. Plant*, Vol. 37, pp. 213–217, (1976) and Bergmann, *Planta*, Vol. 74, pp. 243–249 (1967).

U.S. Pat. No. 3,816,960 describes the effect of several factors, including the presence of one volume percent carbon dioxide, on the photosynthesis and rate of respiration of a callus culture. U.S. Pat. No. 4,326,034 describes a process for the preparation of a culture of higher plant cells capable of growing in the presence of light and in the absence of a carbohydrate carbon source in which the plant cells are initially cultivated in an aqueous medium in the presence of light, carbon dioxide, oxygen, and a maximum concentration of dissolved oxygen in the aqueous medium of 250 n mol per milliliter.

On the other hand, virtually no information is available on what effect, if any, the presence of exogenous carbon dioxide may have on the propagation of plants via organogenesis from tissue cultures. Such an experiment was attempted by Cornejo-Martin, et al., *Zeitschrift Pflanzenphysiologie, Vol.* 74, pp. 177–123 (1979). However, in those experiments, which involved rice callus cultures, it was determined that concentrations of carbon dioxide ranging from 1% to 20% had no effect on shoot regeneration.

According to the present invention, however, it has been found that enhanced shoot regeneration from tissue cultures of solanaceous plants, particularly those obtained by culturing explants from cotyledon tissue, and from callus, is improved by the presence of from about 0.5 to about 2.0% by volume of carbon dioxide in the culture's atmosphere.

SUMMARY OF THE INVENTION

This invention therefore comprises a method of propagating plants from tissue cultures comprising cultivating plant tissue cultures in a nutrient medium appropriate for the propagation of plants therefrom, in the presence of from about 0.5 to about 2.0% by volume carbon dioxide.

DETAILED DESCRIPTION OF THE INVENTION

As will be shown in the examples which follow, a number of factors or considerations exist in carrying out the process in order to produce the desired results, namely shoot and consequent growth enhancement. These factors include, for instance, the types of plants employed, the source from which the tissue culture is obtained, the constituents including plant growth enhancing hormones of the nutrient medium employed, the presence and/or nature of the carbohydrate carbon source, the presence and intensity of light, and the concentration (in volume percent) of carbon dioxide in the atmosphere.

As pointed out above, this process is applicable to the propagation of solanaceous plants from tissue culture. The term "solanaceous plant" refers to members of the family Solanaceae as defined, for instance, in L. H. Bailey, *Manual of Cultivated Plants (MacMillan Pub. Co.,* 1951) at pp. 866–867, including tobacco (*Nicotiana tabacum*) and black nightshade (Solanum nigrum).

The tissue cultures utilized in this process are preferably obtained from cotyledon explants. Alternatively, explants of callus may be used, providing appropriate growth-enhancing hormones are present, as described below. On the other hand, as will be seen from the tables which follow, experiments conducted to data have not succeeded in producing shoots from tobacco root or hypocotyl explants.

The nutrient medium employed may be any of those which are known to be suitable for the cultivation of the tissue cultures in question and the propagation of plants from them. Suitable nutrient media in general, include Murashige and Skoog, White, Heller, Hildebrandt et al., etc. See Murashige, *Ann. Rev. Plant Physiol.*, supra.

Also included in the nutrient medium may be substances which promote the growth of plants, as known in the art, and may be generally designated by the term "hormones". For cotyledon explants, the cultures contained kinetin and indoleacetic acid. These hormones however, when utilized in certain ratios and amounts, as shown in the experiments described below, did not succeed in enhancing the growth of shoots from tobacco callus. However, when callus was grown in nutrient media including indoleacetic acid and isopentenyl adenine, at appropriate ratios as known in the art, shoot initiation occurred.

As shown in the experiments below, shoot formation is enhanced even without the presence of a carbohyrate carbon source. Such was the case when mannitol, which is not a carbon source, was substituted entirely for sucrose, in order to maintain the osmotic potential of the medium. However, best results were observed when the medium contained a carbohydrate carbon source.

The carbohydrate carbon source may similarly be any of those known to be suitable for this purpose in cultivating tissue cultures of this type. Such carbohydrates will include, for instance, sucrose, glucose, and/or fructose. The amount of the carbohydrate in the nutrient medium will generally range up to about 10%, preferably from about 1 to about 3%, in terms of weight per volume of solution (i.e., 3%=30 g/liter of solution). In the case of sucrose, generally up to about 3% sucrose is satisfactory, depending on the other conditions as described below. Mannitol may be partially or completely substituted for the sucrose, as described below.

In general, these types of growing conditions are well known and they, as well as other considerations, are described in more detail in the papers by Murashige, mentioned earlier.

Another condition involved in the carrying out of the process is the presence or absence of light. Tests were variously run at light intensities from 1000 to 6000 lux, and is darkness. In the darkness, as will be described below, the presence of additional carbon dioxide enhanced shoot formation, when this occurred. However, shoot formation did not occur in all experiments carried out under dark conditions. It appears that, with no light present, shoot formation only occurred in the presence of 1% sucrose. Thus, light was also not required to produce shoot formation with this concentration of sucrose. On the other hand, with a concentration of 3% sucrose, shoot enhancement only occurred in the presence of light.

When using cotyledon explants, the seedlings are first grown in darkness, until germinated, which generally requires about 6-8 days, then under light conditions for at least 3-4 days, and preferably about 7 days. If the seedlings are cultivated under light for too short a period, the shoot enhancement effect of the carbon dioxide may not occur.

The carbon dioxide content in the atmosphere can generally range from about 0.5 to about 2.0% and is preferably about 1%, all by volume.

The preferred conditions for carrying out the process include the presence of 1% sucrose as the carbohydrate carbon source, a light intensity of about 1000 to about 2000 (most preferably about 1500) lux and about 1 volume percent carbon dioxide in the atmosphere.

The following examples are intended to illustrate the parameters and methods of carrying out the invention.

GENERAL EXPERIMENTAL PROCEDURE

To obtain the cotyledon, hypocotyl and root explants, seeds were first sterilized in a 10% bleach solution for 15 minutes. The seeds were then germinated in the dark at 26° C. for one weak in tubes containing sterile medium (1% agar and 0.5% sucrose). Next, the seedlings were grown in the light (2000 lux) for one additional week. The explants were then removed.

The explants were grown on Murashige and Skoog medium containing 1% agar and a carbon source and plant growth hormones, as provided in the examples which follow. The constituents of this medium are described in *Plant*, Vol. 15, pp. 473-497 (1962). Callus explants were grown on Murashige and Skoog medium containing 0.8% agar.

Cultures were maintained in controlled incubators at 25° C. with a 16-hour light and 8-hour dark photoperiod. Exogenous $CO_2$ was added to one incubator from a cylinder containing 30% $CO_2$. No $CO_2$ was added to the other incubator. The final concentration of $CO_2$ was estimated using a Drager pump and specific $CO_2$ detector tubes. The pH of the media was tested to verify that the $CO_2$ treatment had not significantly altered the pH. Observations were made after four weeks of culture. At least twenty cultures were utilized in each experiment.

EXAMPLE 1

Tobacoo (*Nicotiana tabacum*) cotyledon, hypocotyl and root explants were transferred onto Murashige and Skoog medium to which was added 3% sucrose, 0.3 mg/l kinetin (K), and 3 mg/l indoleacetic acid (IAA). Half of the samples of each type of explant were cultured at ambient $CO_2$ (0.03%), and the other half at 1% $CO_2$. All samples were exposed to light at an intensity of 6000 lux. The results are given in Table 1.

TABLE 1

| | Average Number of Shoots per Explant | |
|---|---|---|
| Explant Source | Ambient $CO_2$ | 1% $CO_2$ |
| Root | 0 | 0 |
| Cotyledon | 0.05 | 0.35 |
| Hypocotyl | 0 | 0 |

Hypocotyl and root explants did not produce shoots. Tobacco cotyledon explants cultured at 1% $CO_2$ produced more shoots than those cultured at ambient $CO_2$.

EXAMPLE 2

Tobacco cotyledon explants were transplanted onto Murashige and Skoog medium to which was added 3% sucrose, 0.3 mg/l K, and 3 mg/l IAA, and cultured in the dark. Half the explants were exposed to ambient CO and the other half to 1% $CO_2$.

A second group of explants was instead cultured under 6000 lux 2, intensity light at ambient $CO_2$, and the other half at 1% $CO_2$. Results are shown in Table 2.

TABLE 2

| | Ambient $CO_2$ | | 1% $CO_2$ | |
|---|---|---|---|---|
| | Average Number of Shoots/Explant | Callus | Average Number of Shoots/Explant | Callus |
| Light (6000 lux) | 0 | — | 0.43 | — |
| Dark | 0.07 | + | 0 | + |

EXAMPLE 3

Tobacco explants were transferred onto Murashige and Skoog medium with 0.3 mg/l K, 3 mg/l IAA, and 0, 1, or 3% sucrose and cultured in the dark. Results are shown in Table 3.

TABLE 3

| | Ambient $CO_2$ | | | 1% $CO_2$ | | |
|---|---|---|---|---|---|---|
| % Sucrose | Shoots/Explant | Roots | Callus | Shoots/Explant | Roots | Callus |
| 0 | 0 | — | — | 0 | — | — |
| 1 | 0.39 | — | + | 1.07 | — | + |

TABLE 3-continued

| | Ambient CO$_2$ | | | 1% CO$_2$ | | |
|---|---|---|---|---|---|---|
| % Sucrose | Shoots/Explant | Roots | Callus | Shoots/Explant | Roots | Callus |
| 3 | 0.07 | + | + | 0 | + | + |

Shoots were produced at 1% sucrose; furthermore, shoot production at 1% CO$_2$ was enhanced over that at ambient CO$_2$.

EXAMPLE 4

Tobacco cotyledon explants were transferred onto Murashige and Skoog medium with 0.3 mg/l K and 3 mg/l IAA, and 0, 1, or 3% sucrose. In addition, 15.9 g/l mannitol was added to media containing no sucrose, and 10.6 g/l to those with 1% sucrose, in order to make the osmotic potential of each medium equivalent to that of the media containing 3% sucrose. This was done to insure that differences in osmotic potential due to different sucrose concentrations would not influence shoot formation. Different samples of the explants grown at each sucrose concentration were cultured in the dark, under a low light intensity, (1500 lux) and under a higher light intensity (6000 lux). Results are shown in Table 4.

TABLE 4

| | Average Number of Shoots per Explant | | |
|---|---|---|---|
| | | Ambient CO$_2$ | | % of |
| | % Sucrose | Control | 1% CO$_2$ | Control |
| Light (6000 lux) | 0 | 0.03 | 0.07 | 233 |
| | 1 | 0 | 0.27 | — |
| | 3 | 0 | 0 | 0 |
| Light (1500 lux) | 0 | 0.1 | 0.40 | 400 |
| | 1 | 0.93 | 2.67 | 287 |
| | 3 | 0.57 | 1.79 | 314 |
| Dark | 0 | 0 | 0 | 0 |
| | 1 | 0.27 | 0.57 | 211 |
| | 3 | 0.1 | 0.40 | 400 |

Under all conditions, more shoots were produced at 1% CO$_2$ than at ambient CO$_2$. The lower light intensity (1500 lux) was most favorable to shoot production. In the absence of light, sucrose was required for shoot formation.

EXAMPLE 5

Tobacco callus which had previously been grown on Murashige and Skoog medium containing 3% sucrose, 0.3 mg/l K, and 3 mg/l IAA was transferred to the same medium, except with sucrose concentrations of 0, 1, and 3%. The light intensities and CO$_2$ concentrations were also varied as in Example 4. No shoots were produced under any of the conditions.

EXAMPLE 6

Tobacco callus which had been grown on Murashige and Skoog medium containing 3% sucrose, 0.3 mg/l K, and 3 mg/l IAA was transferred to a medium containing 0.3 mg/l IAA and 10 mg/l isopentenyl adenine (2-ip). As in Example 4, samples were subjected to various light intensities, sucrose and mannitol concentrations, and CO$_2$ levels. Results are shown in Table 5. The number of plus (+) signs indicates the relative amounts of additional callus formed.

TABLE 5

| | Ambient CO$_2$ | | | 1% CO$_2$ | | |
|---|---|---|---|---|---|---|
| % Sucrose | # Shoots/Piece | # Roots/Piece | Relative Amount of Callus | # Shoots/Piece | # Roots/Piece | Relative Amount of Callus |
| Light (4000 lux) | | | | | | |
| 0 | 0 | 0 | + | 0.20 | 0 | + |
| 1 | 0.95 | 0 | ++ | 6.38 | 0 | ++ |
| 3 | 1.40 | 0 | +++ | 5.20 | 0 | +++ |
| Light (1000 lux) | | | | | | |
| 0 | 0 | 0 | + | 0 | 0 | + |
| 1 | 0.70 | 0 | ++ | 2.10 | 0.05 | ++ |
| 3 | 0.20 | 0 | +++ | 6.35 | 0 | +++ |
| Dark | | | | | | |
| 0 | 0 | 0 | + | 0 | 0 | + |
| 1 | 0 | 0 | ++ | 0 | 0 | ++ |
| 3 | 1.65 | 0 | +++ | 1.35 | 0.10 | +++ |

In the light, more shoots were produced at 1% CO$_2$ than at ambient CO$_2$. No shoots were produced in the dark from callus explants, except with 3% sucrose, and no enhancement was seen with 1% CO$_2$.

EXAMPLE 7

Black nightshade (*Solanum nigrum*) cotyledon explants from four-day old seedlings were transplanted onto Murashige and Skoog medium plus 0.3 mg/l K and 3 mg/l IAA with 1% sucrose. Mannitol (10.6 g/l) was added to give a molar equivalent to 3% sucrose. The explants were cultured in light (1500 lux) at ambient and 1% CO$_2$. More shoots were produced at 1% than at ambient CO$_2$.

TABLE 6

| | Ambient CO$_2$ Control | 1% CO$_2$ | % of Control |
|---|---|---|---|
| Average Number of Shoots/Cotyledon | 0.38 | 1.00 | 263 |
| Average Number of Roots/Cotyledon | 0.21 | 0.62 | 295 |

What is claimed is:

1. A method of propagating tobacco plants from tissue cultures of cotyledon or callus explants by subjecting said tissue culture to propagation enhancement conditions in the presence of an appropriate nutrient medium, in which the propagation is conducted in the presence of from about 0.5 to about 2.0% by volume of carbon dioxide in the atmosphere, and, if the propagation is carried out in the absence of light, the nutrient medium contains 1% of a carbohydrate carbon source.

2. A method according to claim 1 in which the carbohydrate carbon source is sucrose.

3. A method according to claim 1 in which the propagation is conducted in the presence of light in an intensity of from about 1,000 to about 6,000 lux.

4. A method according to claim 3 in which the propagation is carried out in the presence of light in an intensity of from about 1,000 to about 2,000 lux, 1% sucrose, and about one volume percent carbon dioxide.

* * * * *